(12) United States Patent
Okihara

(10) Patent No.: US 6,362,474 B1
(45) Date of Patent: Mar. 26, 2002

(54) SEMICONDUCTOR SAMPLE FOR TRANSMISSION ELECTRON MICROSCOPE AND METHOD OF MANUFACTURING THE SAME

(75) Inventor: Masao Okihara, Miyagi pref. (JP)

(73) Assignee: Oki Electric Industry Co., Ltd., Tokyo (JP)

( * ) Notice: Subject to any disclaimer, the term of this patent is extended or adjusted under 35 U.S.C. 154(b) by 0 days.

(21) Appl. No.: 09/386,369

(22) Filed: Aug. 31, 1999

(30) Foreign Application Priority Data

Oct. 19, 1998 (JP) .......................................... 10-295952

(51) Int. Cl.[7] ........................ H01J 37/317; H01J 37/305
(52) U.S. Cl. ........................ 250/304; 250/311; 250/404; 250/492.2; 250/492.21; 438/494
(58) Field of Search .................................. 250/304, 311, 250/404, 492.2, 492.21; 438/494

(56) References Cited

U.S. PATENT DOCUMENTS

| | | | |
|---|---|---|---|
| 5,270,552 A | * 12/1993 | Ohnishi et al. | 250/307 |
| 5,583,344 A | * 12/1996 | Mizumura et al. | 250/492.21 |
| 5,656,811 A | 8/1997 | Itoh et al. | 250/309 |
| 5,681,616 A | * 10/1997 | Gupta et al. | 427/264 |

* cited by examiner

Primary Examiner—Bruce Anderson
Assistant Examiner—Nikita Wells
(74) Attorney, Agent, or Firm—Junichi Mimura

(57) ABSTRACT

Described here is a method of forming a thin-film portion for allowing electrons produced from a transmission electron microscope to pass therethrough at a portion to be observed of a semiconductor and effecting a predetermined etching process on the thin-film portion thereby to create a semiconductor sample for the transmission electron microscope. Prior to the execution of the etching process, grooves for reducing a stress introduced into the thin-film portion by the etching process are defined in the thin-film portion.

6 Claims, 5 Drawing Sheets

SEMICONDUCTOR SAMPLE FOR TRANSMISSION ELECTRON MICROSCOPE AND METHOD OF MANUFACTURING THE SAME

BACKGROUND OF THE INVENTION

1. Field of the Invention

This invention relates to a semiconductor sample suitable for a transmission electron microscope (hereinafter called simply "TEM"), which is to be observed by the TEM and a method of manufacturing the semiconductor sample.

2. Description of the Related Art

It is of importance to recognize in detail the state of distribution of impurities in an impurity diffusion region for semiconductor devices like MOS transistors incorporated into a semiconductor substrate as components of a semiconductor integrated circuit in order to evaluate and analyze the semiconductor integrated circuit.

A TEM is known as one of means for observing the impurity diffusion region, etc. in such a semiconductor substrate.

In order to observe a semiconductor by the TEM, a thin-film portion for allowing an electron beam to pass therethrough is formed in the semiconductor to be observed. The thin-film portion is formed at an edge portion of the semiconductor by beam-based grinding processing using a focused ion beam device (hereinafter called simply as "FIB"), for example.

Prior to the observation of the thin-film portion by the TEM, the entire semiconductor including the surface of the thin-film portion is subjected to a selective etching process using an etchant. The selective etching process makes it possible to selectively remove a lattice defective portion produced due to impurities in the thin-film portion, etc., whereby an impurity distribution can be observed by the TEM for the first time.

Meanwhile, according to the above-described conventional method of manufacturing the sample, the thin-film portion formed integrally with the edge portion of the semiconductor at the edge portion thereof is provided in continuation with a main body of the semiconductor in a region excluding the edge portion. Therefore, since a large stress is concentrated on the thin-film portion when the entire semiconductor including the thin-film portion is subjected to the selective etching process, bending distortion has occurred in the thin-film portion due to the stress.

The bending distortion of the thin-film portion results in the creation of stripe-like contrast in an image observed by the TEM, thus causing a hindrance to a good-quality TEM image.

SUMMARY OF THE INVENTION

Thus, an object of the present invention is to provide a semiconductor sample free from the introduction of bending distortion into a thin-film portion owing to selective etching corresponding to pre-treatment, and a method of manufacturing the semiconductor sample.

According to one aspect of this invention, there is provided a semiconductor sample manufacturing method, comprising the following steps of:

forming a thin-film portion for allowing electrons produced from a transmission electron microscope to pass therethrough at a portion to be observed of a semiconductor;

thereafter subjecting the thin-film portion to a predetermined etching process thereby to manufacture a semiconductor sample for the transmission electron microscope; and defining grooves for reducing a stress introduced into the thin-film portion by the etching process in the thin-film portion prior to the execution of the etching process.

According to the present invention, even if the conventional stress is produced in the semiconductor including the thin-film portion by the etching process, the grooves defined in the thin-film portion substantially absorb a stress that acts on the thin-film portion. Therefore, the conventional concentration of stress on the thin-film portion is prevented from occurring, so that the thin-film portion is prevented from being deformed due to the stress concentration.

Typical ones of various inventions of the present application have been shown in brief. However, the various inventions of the present application and specific configurations of these inventions will be understood from the following description.

BRIEF DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

DETAILED DESCRIPTION OF THE PREFERRED EMBODIMENTS

The present invention will hereinafter be described in detail by illustrated preferred embodiments.

SPECIFIC EXAMPLE 1

Figure 1:
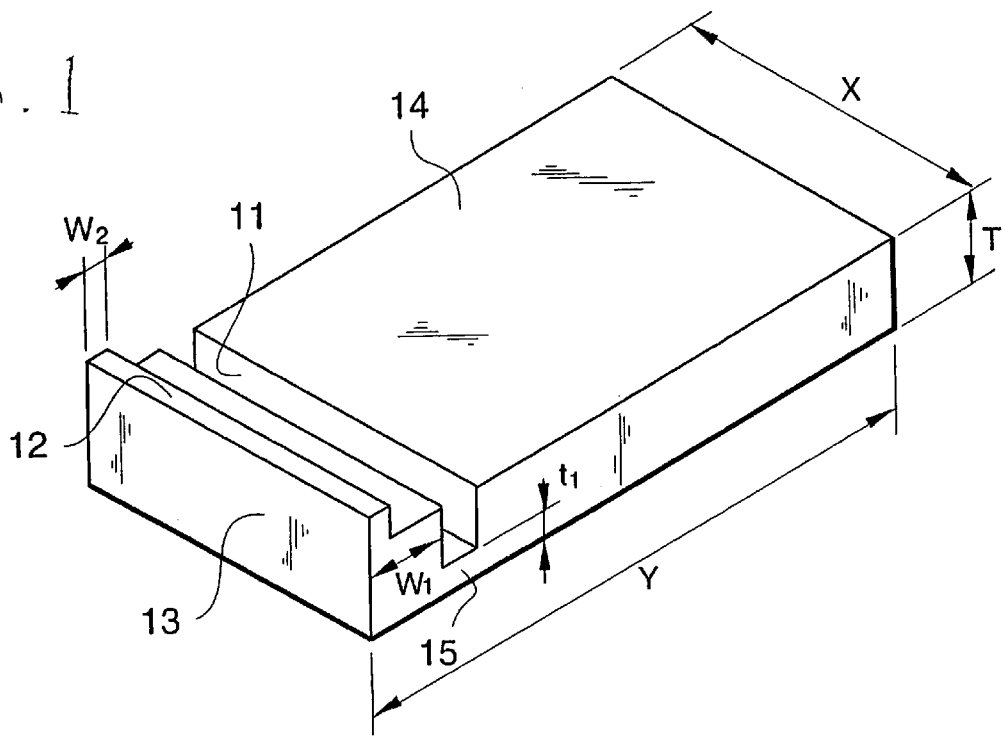
FIG. 1 is a perspective view showing one process step of a method of manufacturing a semiconductor sample according to the present invention.

FIG. 1 shows one process step of a method for manufacturing a sample for a transmission electron microscope, according to the present invention.

In the illustrated example, for example, a silicon semiconductor substrate 10 is used which has a longitudinal dimension Y of about 11 mm, a transverse dimension X of about 3 mm and a thickness dimension T of about 0.5 mm and is shaped in the form of a rectangular parallelepiped over its entirety.

A separating slit 11 extending along the transverse direction (X) of the silicon semiconductor substrate 10 is defined in the surface of the silicon semiconductor substrate 10. Owing to the slit 11, the silicon semiconductor substrate 10 is partitioned into a sample region 13 with a rising edge portion 12 having an impurity region, for example, corresponding to a portion to be inspected, and a dummy region 14 for making it easy to treat the semiconductor substrate 10 including the sample region 13.

A thickness dimension $t_1$ of a thin-wall portion 15 of the semiconductor substrate 10, which has left behind owing to the provision of the slit 11, may preferably be set to approximately 0.2 mm to facilitate separation resultant from a cleavage developed between the sample region 13 and the dummy region 14 to be described later.

The sample region 13 has a width dimension $W_1$ of about 0.5 mm. Further, the sample region 13 has the rising edge portion 12 provided on one side thereof in the transverse direction thereof so as to extend in the longitudinal direction of the sample region 13 with a width dimension $W_2$ of 40 μm, for example.

A length dimension of the dummy region 14 along the longitudinal dimension Y may preferably be set to approximately 10 mm to facilitate the handling of the semiconductor substrate 10.

Figure 2:
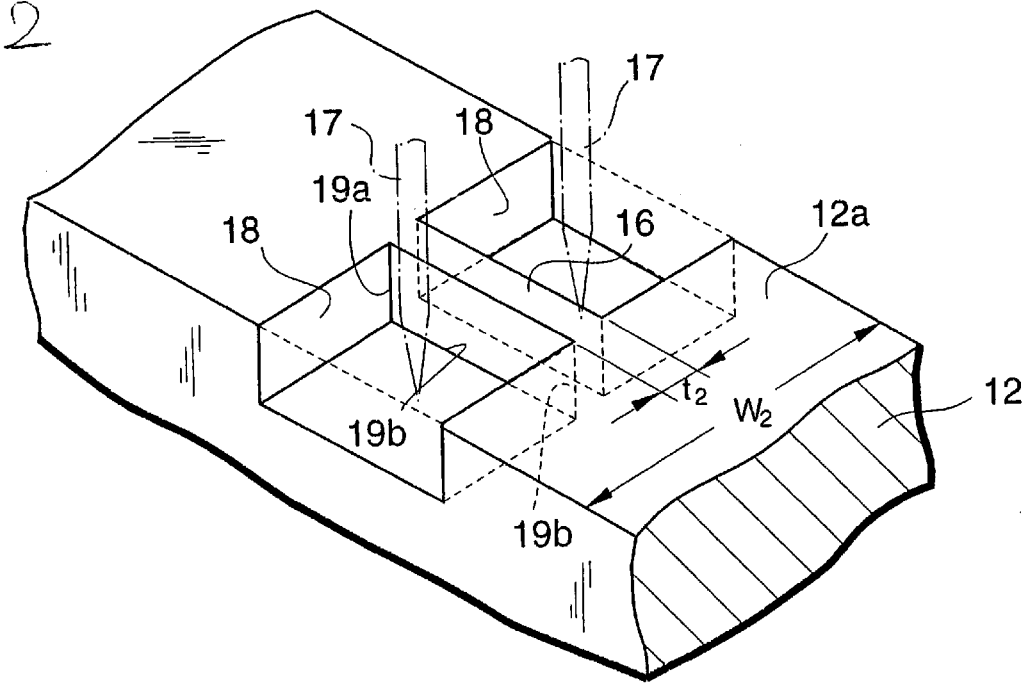
FIG. 2 is a perspective view, partly in enlarged form illustrating a process step for forming a thin-film portion of the semiconductor sample according to the present invention.

FIG. 2 shows a process step for forming a thin-film portion in the sample region 13.

As shown in FIG. 2, a thin-film portion 16 having a thickness dimension $t_2$ of 0.2 μm, for example, is formed in the sample region 13.

As has conventionally been well known, the thin-film portion 16 can be formed by applying convergent or focused beams 17 each composed of, for example, a Ga ion produced from an unillustrated FIB device from the upper edge side of the rising edge portion 12 to both sides thereof.

Owing to the application of the focused beams 17 to the rising edge portion 12, a pair of rectangular concave portions 18 and 18 with the upper edge of the rising edge portion 12 as one side is defined in both sides of the rising edge portion 12 as viewed along the transverse direction ($W_2$) of the rising edge portion as has conventionally been well known. Thus, the thin-film portion 16 having a thickness dimension $t_2$ which is an approximately uniform thickness dimension and extends in the direction coincident with the transverse direction ($W_2$) of the rising edge portion 12, is defined between both the concave portions 18.

The thin-film portion 16 has bases 19a and a pair of sides 19b connected to the sample region 13 excluding the thin-film portion 16, i.e., a sample body (13). The two sides 19b extend toward their corresponding bases 19a substantially at right angles to an outer edge 12a of the rising edge portion 12 from the top face 12a of the rising edge portion 12, i.e., the outer edge 12a thereof.

Means other than the focused beams 17 produced from the above-described FIB device can be utilized to form the thin-film portion 16. It is however desirable to use the focused beams 17 produced from the FIB device with a view toward forming a thin-film portion 16 having a desired thickness dimension $t_2$ with high accuracy.

Upon attachment of the semiconductor substrate 10 to the FIB device, the semiconductor substrate 10 is placed on a conductive sample table with an auxiliary material such as silver paste for increasing conductivity interposed therebetween in order to prevent the semiconductor substrate 10 from being charged up due to the application of the focused beams 17. The application of the auxiliary material to the dummy region 14 upon application of the auxiliary material to the semiconductor substrate 10 makes its possible to prevent the sample region 13 from being contaminated due to the auxiliary material.

The thin-film portion 16 can be formed prior to the formation of the slit 11. The front and back of its procedure can be suitably determined.

Figure 3:
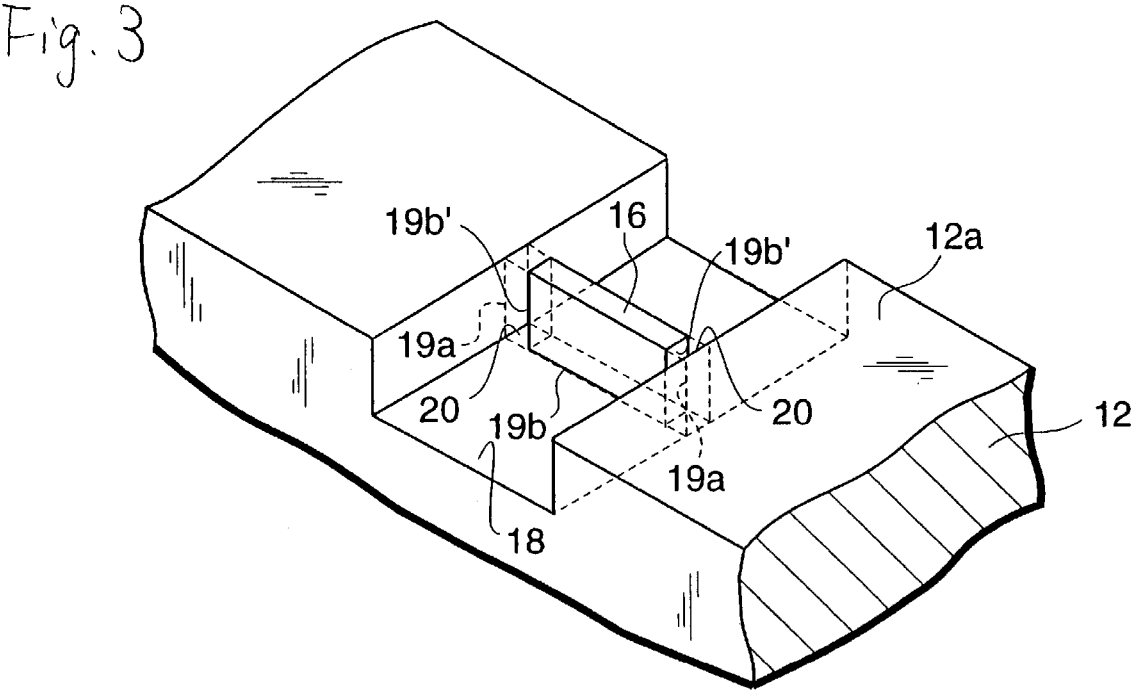
FIG. 3 is a view similar to FIG. 2, depicting a process step for defining grooves in the thin-film portion of the semiconductor sample according to the present invention.

FIG. 3 shows a process step for introducing grooves into the thin-film portion 16.

After the formation of the thin-film portion 16, stress-relieving grooves 20 are defined in the thin-film portion 16 along their corresponding sides 19b in an example illustrated in FIG. 3. The grooves 20 can be defined by using the focused beams 17 produced from the FIB device.

The pair of grooves 20 is interposed between the sample body (13) and the thin-film portion 16 by extending the grooves 20 along the sides 19b continuously connected to the sample body (13) of the thin-film portion 16, whereby additional side edge portions 19b' of the thin-film portion 16 are defined.

As a result, both side edge portions 19b' of the thin-film portion 16 are sectioned from the sample body (13) by the pair of grooves 20. Further, the thin-film portion 16 is provided in continuation with the sample region 13, i.e., the sample body (13) only by the bases 19a paired with one sides coincident with the outer edge 12a of the rising edge portion 12.

In order to selectively remove an impurity diffusion region of the thin-film portion 16 to be observed after the formation of the grooves 20 in the thin-film portion 16, the sample body (13) including the thin-film portion 16, i.e., the sample region 13 is immersed into a selective etchant over its entirety.

Upon the handling of the semiconductor substrate 10 for this selective etching process, the dummy region 14 of the semiconductor substrate 10 can be nipped with a pincette or the like, for example. The nipping of the dummy region 14 by the pincette makes it possible to prevent the sample region 13 including the observed portion from being damaged due to its handling and execute a reliable and easy etching process.

Since a metal portion other than the semiconductor substrate 10 does not touch the etchant upon the etching process, the sample region can be assuredly prevented from being contaminated due to the etching of the metal portion.

Such a strong stress similar to the conventional example as to produce a bend in the thin-film portion 16 is developed in the sample body (13) including the thin-film portion 16 while the etching process is being executed.

In the method according to the invention of the present application, however, since the thin-film portion 16 subjected to the selective etching process is not restrained by or locked to the sample body (13) with the bases 19a and the pair of sides 19b as in the conventional example and is provided in continuation with or connected to the sample body (13) by the bases 19a alone, edge portions extending in three directions, including the pair of sides 19b' serve as free edge portions free of restraint.

Therefore, even if the strong stress acts on the sample body (13), it is not transferred to the thin-film portion 16 as in the conventional example. Further, the stress that acts on the thin-film portion 16, is relieved due to temporary deformation of the thin-film portion 16. Therefore, no strong stress remains in the thin-film portion 16 and strong bending deformation due to the remaining stress is no longer produced.

Thus, the conventional strong bending deformation is not produced in the thin-film portion 16 owing to the above-described selective etching process.

Figure 4:
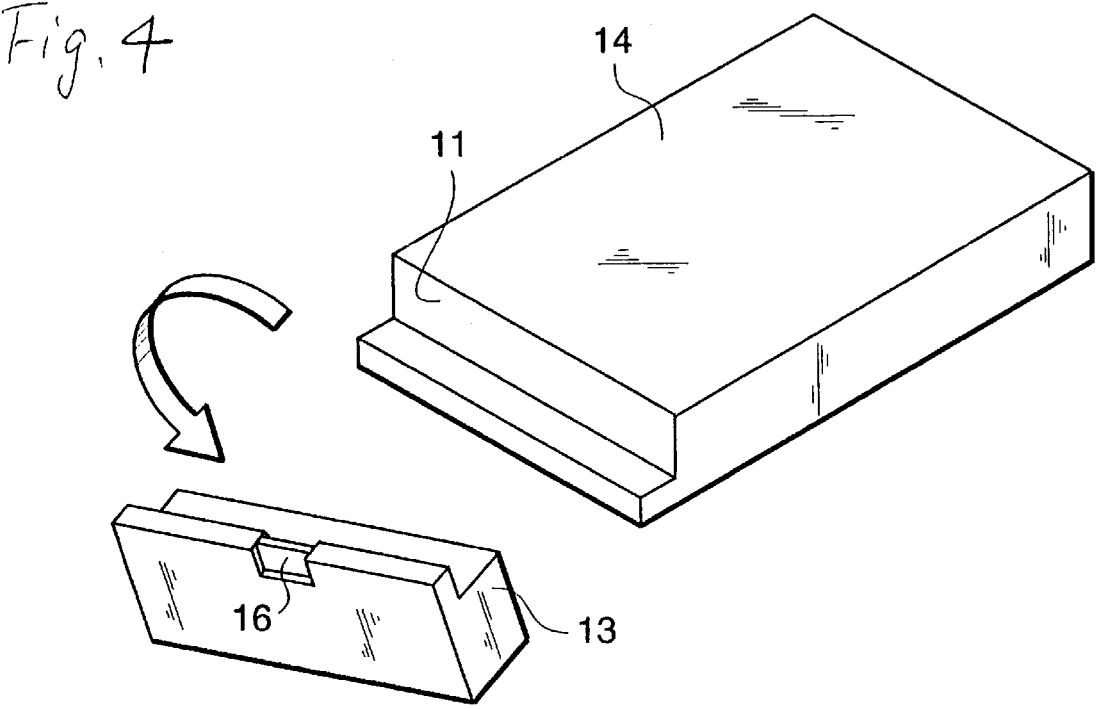
FIG. 4 is a perspective view showing a process step for separating a sample region of the semiconductor sample according to the present invention.

In the semiconductor substrate 10 including the sample body (13) subjected to the selective etching process, the sample body (13) including the thin-film portion 16 is separated from the semiconductor substrate 10 by the cleavage using the slit 11 as shown in FIG. 4. The separated sample body (13) is placed on a metal holder 21 composed of a metallic mesh as shown in FIG. 5.

Figure 5:
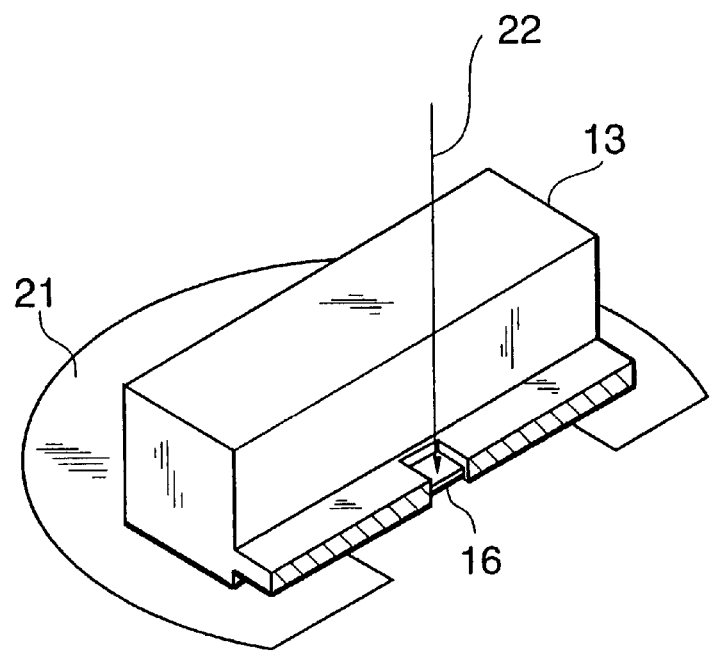
FIG. 5 is a perspective view illustrating a state of completion of the semiconductor sample according to the present invention.

As indicated by an arrow 22 in FIG. 5, an electron beam is transmitted through the thin-film portion 16 of the sample body (13) placed in an unillustrated TEM via the metal holder 21.

Since the conventional large bending deformation due to the stress is not produced in the thin-film portion 16 while image contrast is obtained due to a diffraction effect of the transmitted light as a principal, interference fringes incident to the bending deformation do not occur in the image contrast.

Thus, according to the method of the present invention, a semiconductor sample, which causes no interference fringes due to the bending deformation of the thin-film portion 16, can be formed with relative ease. According to the semiconductor sample related to the present invention as well, a clear TEM image excluding such interference fringes can be obtained.

The embodiment described above shows as an example the case in which the grooves 20 for relieving the stress are defined along the pair of sides 19b to set the three-direction edge portions of the thin-film portion 16 as the free edges free from restraint of the sample body (13). As an alternative to this example, however, stress-relieving grooves (20) can be defined along both edges of one side 19b and the base 19a respectively.

Further, one groove (20) can be formed along the edge of either one side 19b or the side 19b. According to this, two-direction edge portions of the thin-film portion 16 can be formed as free edges. It is however desirable that the three-direction edge portions of the thin-film portion 16 are formed as the free edges as described above to improve the effect of reducing the stress applied to the thin-film portion 16 by the selective etching.

When the thin-film portion 16 is subjected to the beams produced from the FIB device in the process step for forming the thin-film portion 16 and the process step for defining the grooves 20, an amorphous layer indicative of resistance to the subsequent selective etching might be formed on the surface of the thin-film portion 16.

The amorphous layer will result in a reduction in the efficiency of the subsequent selective etching process. Further, etching characteristics vary due to such variations in the etching efficiency. It is therefore desired that the amorphous layer formed on the surface of the thin-film portion 16 is removed in advance by ion-milling using an ion such as Ar or the like prior to the selective etching process with a view toward improving the efficiency of the selective etching process and obtaining uniform etching characteristics.

SPECIFIC EXAMPLE 2

FIGS. 6 through 9 respectively show a sample manufacturing method according to the present invention, which makes no use of the dummy region referred to above.

Figure 6:
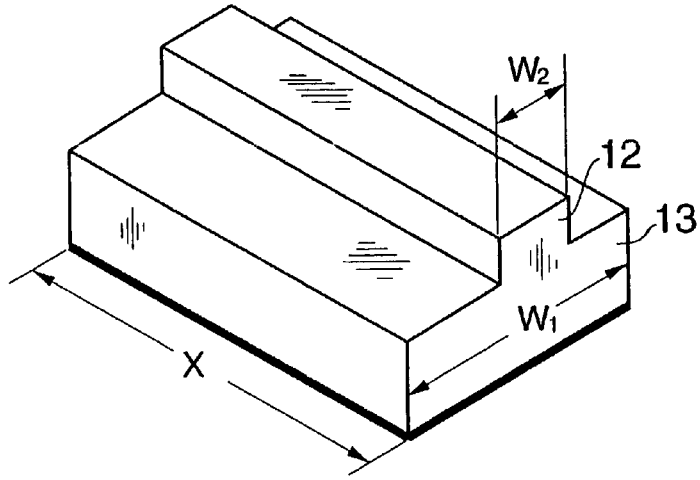
FIG. 6 is a perspective view depicting one process step of another method of manufacturing a semiconductor sample according to the present invention.

As shown in FIG. 6, a sample body 13 is formed which comprises, for example, a silicon semiconductor which has a rising edge portion 12 similar to the above, having, for example, a transverse dimension $W_2$ of 40 $\mu$m and a longitudinal dimension X of 3 mm and which is shaped in the form of a rectangular parallelopiped over its entirety. A transverse dimension $W_1$ of the sample body 13 can be set to 0.5 mm, for example.

Figure 7:
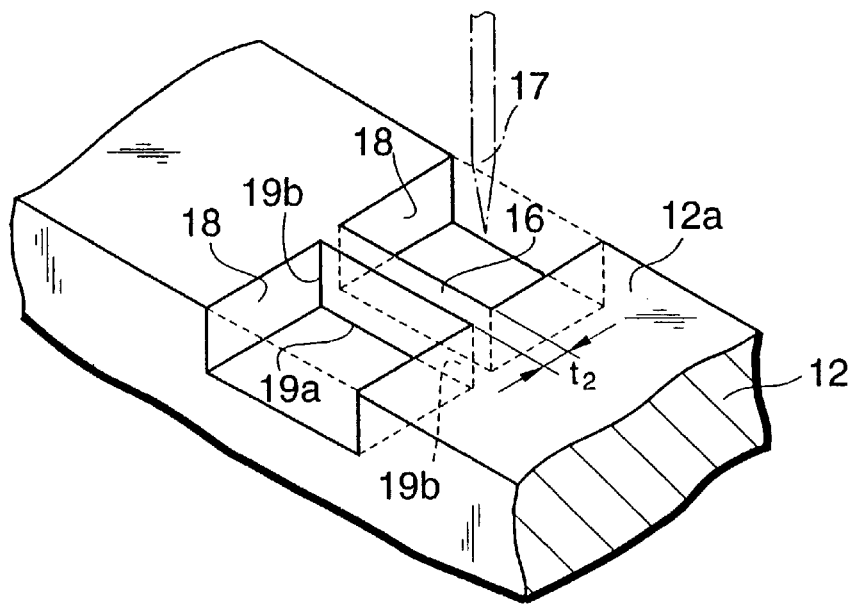
FIG. 7 is a view similar to FIG. 2, showing a process step for forming a thin-film portion of the semiconductor sample shown in FIG. 6.

As shown in FIG. 7, a pair of concave portions 18 is defined in the rising edge portion 12 of the sample body 13 by means of focused beams 17 produced from an FIB device similar to one described in line with the specific example 1, whereby a thin-film portion 16 is defined between both concave portions 18.

A thickness dimension $t_2$ of the thin-film portion 16 can be set to 0.2 $\mu$m, for example in a manner similar to the specific example 1.

Figure 8:
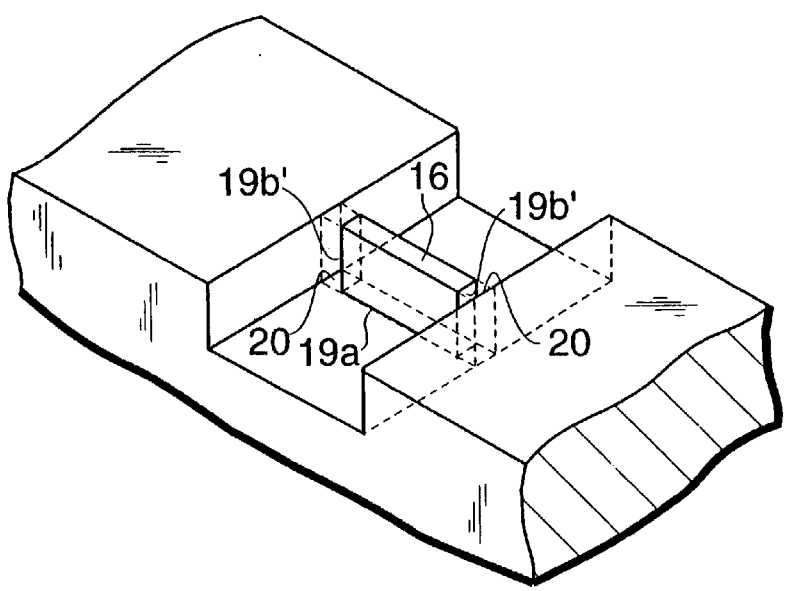
FIG. 8 is a view similar to FIG. 3, illustrating a process step for defining grooves in the thin-film portion shown in FIG. 7.

After the formation of the thin-film portion 16, stress-relieving grooves 20 similar to ones referred to above are defined in the thin-film portion 16 along a pair of sides 19b by means of the focused beams 17 similar to the above as shown in FIG. 8.

Owing to the formation of the grooves 20, both sides 19b of the thin-film portion 16 are separated from the sample body 13 so as to serve as free edges 19b' free from restraint of the sample body 13.

Figure 9:
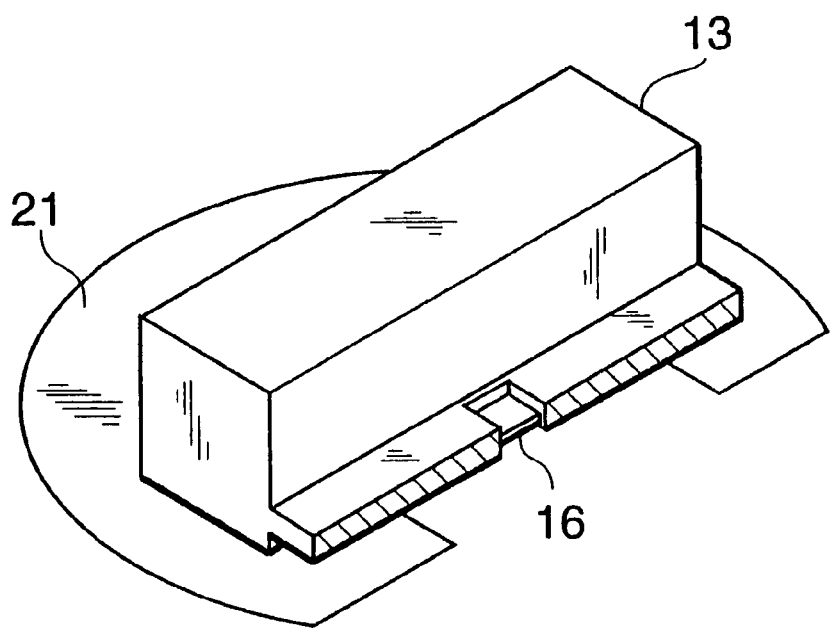
FIG. 9 is a perspective view showing a semiconductor sample subjected to the definition of the grooves shown in FIG. 8 and prior to being subjected to a selective etching process.

While the thin-film portion 16 is subjected to a selective etching process similar to the above, the sample body 13 with the grooves 20 defined therein is attached to a metal holder 21 as shown in FIG. 9 to facilitate the handling of the sample body 13 in the etching process.

Since the selective etching process can be effected on the thin-film portion 16 of the sample body 13 attached to the metal holder 21 according to the handling of the metal holder 21, the sample body 13 including the thin-film portion 16 serving as a portion to be observed can be assuredly prevented from being subjected to damage resulting from the handling of the sample body.

When the metal holder 21 touches a selective etchant upon the selective etching process of the sample body 13, it is subjected to erosion. When the metal holder 21 is subjected to erosion and the metallic material subjected to erosion is attached to the thin-film portion 16, the thin-film portion 16 corresponding to the portion to be observed might be contaminated by such an adherent.

It is considered that the metal holder 21 is formed by a resin material exhibitive of an etching resistant characteristic to reliably prevent such contamination.

Since, however, the resin material having the etching resistant characteristic normally exhibits electrical insulating properties, means for solving charge-up similar to that developed in the FIB device is needed when the sample body 13 is incorporated into a TEM by using such a holder.

While the metal holder 21 is used as shown in FIGS. 1 through 5 from these points of view, the optimal one is the method described in the specific example 1 using the dummy region 14 which does not bring about contamination of the sample body 13 due to the erosion of the metal holder 21.

While the sample for the TEM, for observing the distribution of impurity diffusion of the silicon semiconductor has been described above, the invention of the present application can be applied to various observations by other semiconductor TEM.

According to the manufacturing method related to the present invention, the stress that will act on the thin-film portion with the selective etching process for pretreatment, is substantially absorbed by the grooves defined in the thin-film portion as described above. Thus, the concentration of stress on the thin-film portion as is the case in the conventional example is prevented from occurring and the thin-film portion is prevented from deforming due to the stress concentration. As a result, a semiconductor sample free of the introduction of bending distortion into the thin-film portion can be manufactured with relative ease.

Further, according to the semiconductor sample related to the present invention, since the bending distortion due to pre-treatment is not introduced into the thin-film portion to be observed by the TEM, a good-quality TEM image free from the occurrence of stripe-like contrast due to the bending distortion of the thin-film portion can be obtained.

While the present invention has been described with reference to the illustrative embodiments, this description is not intended to be construed in a limiting sense. Various modifications of the illustrative embodiments, as well as other embodiments of the invention, will be apparent to those skilled in the art on reference to this description. It is therefore contemplated that the appended claims will cover any such modifications or embodiments as fall within the true scope of the invention.

What is claimed is:

1. A semiconductor sample suitable for a transmission electron microscope, comprising:

a main body integrally provided with a thin-film portion for allowing electrons produced from the transmission electron microscope to pass therethrough; and grooves for relieving distortion produced due to a stress introduced into said thin-film portion upon an etching process subjected to said thin-film portion after the formation of said thin-film portion, said grooves being defined in association with said thin-film portion.

2. The semiconductor sample according to claim 1, wherein said grooves are respectively provided between said main body and said thin-film portion and define at least parts of said thin-film portion.

3. A semiconductor sample manufacturing method, comprising the following steps of:

forming a thin-film portion for allowing electrons produced from a transmission electron microscope to pass therethrough at a portion to be observed of a semiconductor;

thereafter subjecting the thin-film portion to a predetermined etching process thereby to manufacture a semiconductor sample for the transmission electron microscope; and defining grooves for reducing a stress introduced into said thin-film portion by the etching process in said thin-film portion prior to the execution of the etching process.

4. A method of manufacturing a semiconductor sample, comprising the following steps of:

defining separation grooves for facilitating separation of the semiconductor sample from a semiconductor substrate thereby to partition the semiconductor substrate into a sample region and a dummy region for facilitating the handling of the semiconductor substrate;

forming a thin-film portion for allowing electrons produced from a transmission electron microscope to pass therethrough at an edge portion of the partitioned sample region;

defining grooves for reducing a stress introduced into the thin-film portion by an etching process subjected to the thin-film portion in the thin-film portion prior to the etching process; and separating the sample region from the dummy region as the semiconductor sample after the etching process.

5. The method according to claim 4, wherein said thin-film portion is defined between a pair of concave portions by means of the concave portions each shaped in the form of a rectangle over its entirety with each outer edge of the edge portion of the sample region as one side within a plane as viewed in the direction of the thickness of the thin-film portion and defined in the sample region on both sides of the thin-film portion, and said grooves defined in the thin-film portion comprise a pair of grooves extending in the direction to be away from each outer edge of the edge portion along a pair of sides of the rectangle extending at a right angle from the outer edge of the edge portion of the sample region.

6. The method according to claim 5, wherein said pair of concave portions for the formation of the thin-film portion and said pair of grooves defined in the thin-film portion are defined by application of ion beams produced from a focused ion beam device.

\* \* \* \* \*